(12) United States Patent
Chen et al.

(10) Patent No.: US 8,501,101 B2
(45) Date of Patent: Aug. 6, 2013

(54) GAS SENSOR

(75) Inventors: I-Cherng Chen, Hsinchu (TW);
Nai-Hao Kuo, Kaohsiung County (TW);
Arthur Lin, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 228 days.

(21) Appl. No.: 12/979,310

(22) Filed: Dec. 27, 2010

(65) Prior Publication Data

US 2012/0138459 A1      Jun. 7, 2012

(30) Foreign Application Priority Data

Dec. 3, 2010   (TW) ................................ 99142176 A (51) Int. Cl.
 *G01N 15/06*     (2006.01)
 *G01N 33/00*     (2006.01)
 *G01N 33/48*     (2006.01)

(52) U.S. Cl.
 USPC ................... 422/83; 422/94; 422/95; 422/96; 422/97; 422/98

(58) Field of Classification Search
 USPC .............................. 422/83, 94, 95, 96, 97, 98
 See application file for complete search history.

(56) References Cited

U.S. PATENT DOCUMENTS

| | | | |
|---|---|---|---|
| 5,310,610 A | 5/1994 | Furubayashi et al. | |
| 5,659,127 A | 8/1997 | Shie et al. | |
| 5,801,070 A | 9/1998 | Zanini-Fisher et al. | |
| 6,161,421 A | 12/2000 | Fang et al. | |
| 6,997,040 B1 | 2/2006 | Lee et al. | |
| 7,276,745 B2 | 10/2007 | Nakagawa et al. | |
| 2007/0212263 A1* | 9/2007 | Shin et al. | 422/95 |

FOREIGN PATENT DOCUMENTS

| | | |
|---|---|---|
| JP | 64-035352 | 2/1989 |
| JP | 10-132957 | 5/1998 |
| JP | 10-148624 | 6/1998 |
| JP | 10-300705 | 11/1998 |
| JP | 11-108874 | 4/1999 |
| JP | 2004-093470 | 3/2004 |
| JP | 2004-093471 | 3/2004 |
| JP | 2004-093475 | 3/2004 |

(Continued)

OTHER PUBLICATIONS

Huff et al., "A Thermally Isolated Microstructure Suitable for Gas Sensing Applications", Tech Digest IEEE Solid State Sens Actuator Workshop (Jun. 6-9, 1988) 47-50.

(Continued)

*Primary Examiner* — Brian J Sines
(74) *Attorney, Agent, or Firm* — Jianq Chyun IP Office (57) ABSTRACT

A gas sensor is provided. The substrate of the gas sensor has a first surface, a second surface and a cavity. The cavity has an opening at the first surface. An insulating film is disposed on the first surface and covers the opening. A heating unit is embedded in the insulating film and located above the opening. An electrode pair is disposed on the insulating film and electrically separated from the heating unit. A buffer layer is disposed on the insulating film and located above the heating unit. The buffer layer is electrically connected to the electrode pair, and at least part of an orthogonal projection of the buffer layer on the first surface is located on the substrate next to the opening. The gas sensing layer is disposed on the buffer layer and has a nano-catalyst therein.

14 Claims, 8 Drawing Sheets

FOREIGN PATENT DOCUMENTS

| | | |
|---|---|---|
| TW | 304307 | 5/1997 |
| TW | I237112 | 8/2005 |
| TW | I278619 | 4/2007 |
| TW | I323344 | 4/2010 |
| TW | I324678 | 5/2010 |

OTHER PUBLICATIONS

Elmi et al., "Optimization of a wafer-level process for the fabrication of highly reproducible thin-film MOX sensors", Sensors and Actuators, B 131 (Feb. 19, 2008) 548-555.

Palzer et al., "Nano- and microsized metal oxide thin film gas sensors", Microsyst Technol (Mar. 4, 2008) 14: 645-651.

Friedberger et al., "Micromechanical fabrication of robust low-power metal oxide gas sensors", Sensors and Actuators B 93 (Aug. 1, 2003) 345-349.

Ralble et al., "Wafer Level Packaging of Micro-Machined Gas Sensors", Sensors, 2004, Proceedings of IEEE, vol. 2 (Oct. 24-27, 2004) 746-748.

* cited by examiner

GAS SENSOR

CROSS-REFERENCE TO RELATED APPLICATION

This application claims the priority benefit of Taiwan application serial no. 99142176, filed on Dec. 3, 2010. The entirety of the above-mentioned patent application is hereby incorporated by reference herein and made a part of this specification.

BACKGROUND OF THE INVENTION

1. Technical Field

The disclosure relates to a gas sensor, in particular, to a gas sensor having nano-catalyst.

2. Background

A gas sensor is a device having important meaning for human life and health. Demands for gas detection are wide, for example, in the fields of home environment monitoring, industrial safety, and disease diagnosis and treatment. Moreover, due to the requirements for industrial safety and environmental regulations, the gas sensor plays an important role. A micro gas sensor is formed by a micro heater in combination with metal oxides with high weather resistance. Low-cost metal oxides are semiconductor-type sensing material, and have good weather resistance and high sensitivity. The micro gas sensor fabricated by a microelectromechanical process has the advantages of small volume, low power consumption, and convenient combination with a microprocessor to form a portable monitor, and thus is superior to conventional expensive and complicated analytical instruments. Therefore, the development of power-saving micro gas sensor is a trend worldwide. However, the micro gas sensor always fails due to long-term high working temperature, as it must operate at a high temperature to have good sensitivity.

SUMMARY

According to an embodiment, a gas sensor is introduced herein, which includes a substrate, an insulating film, a heating unit, an electrode pair, a buffer layer, and a gas sensing layer. The substrate is provided with a first surface, a second surface opposite to the first surface, and a cavity. The cavity is provided with an opening at the first surface. The insulating film is disposed on the first surface and covers the opening. The heating unit is embedded in the insulating film and located above the opening. The electrode pair is disposed on the insulating film and electrically separated from the heating unit. The buffer layer is disposed on the insulating film and located above the heating unit. The buffer layer is electrically connected to the electrode pair, and at least part of an orthogonal projection of the buffer layer on the first surface is located on the substrate next to the opening. The gas sensing layer is disposed on the buffer layer, and the gas sensing layer is provided with a nano-catalyst therein.

In view of the above, according to the gas sensor in the disclosure, the buffer layer is used to enhance the overall mechanical strength and improve the sensing sensitivity.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
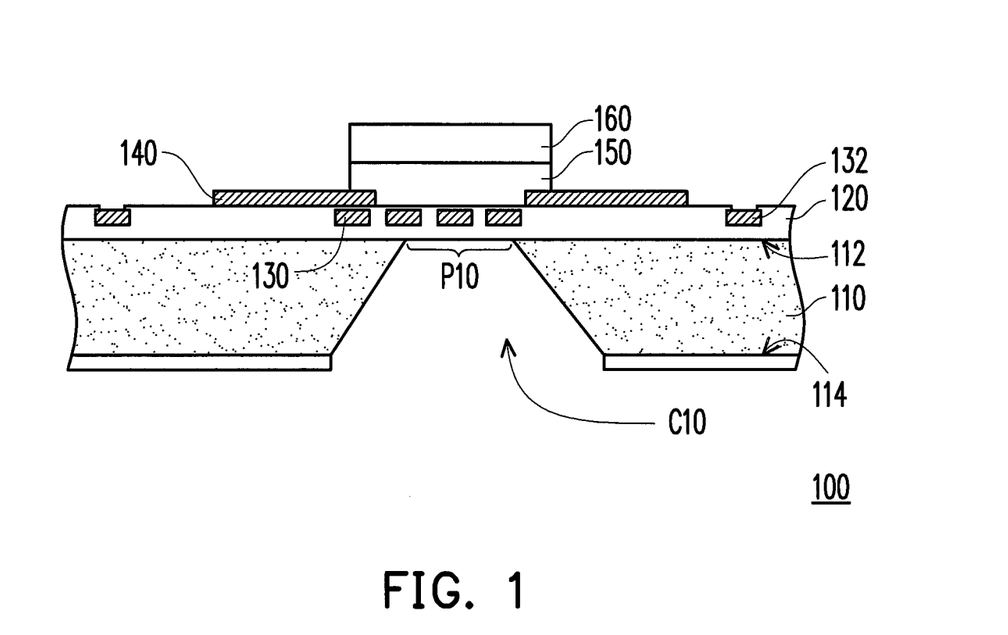
FIG. 1 is a cross-sectional view of a gas sensor according to an embodiment of the disclosure.

FIG. 1 is a cross-sectional view of a gas sensor according to an embodiment of the disclosure. Referring to FIG. 1, a gas sensor 100 includes a substrate 110, an insulating film 120, a heating unit 130, an electrode pair 140, a buffer layer 150, and a gas sensing layer 160. The substrate 110 is provided with a first surface 112, a second surface 114 opposite to the first surface 112, and a cavity C10. The cavity C10 is provided with an opening P10 at the first surface 112. The insulating film 120 is disposed on the first surface 112 of the substrate 110 and covers the opening P10. The heating unit 130 is embedded in the insulating film 120 and located above the opening P10. The electrode pair 140 is disposed on the insulating film 120 and electrically separated from the heating unit 130. The buffer layer 150 is disposed on the insulating film 120 and located above the heating unit 130. The buffer layer 150 is electrically connected to the electrode pair 140, and at least part of an orthogonal projection of the buffer layer 150 on the first surface 112 is located on the substrate 110 next to the opening P10. The gas sensing layer 160 is disposed on the buffer layer 150 and is provided with a nano-catalyst therein.

The gas sensing layer 160 of the gas sensor 100 is capable of sensing different gases due to different types of the nano-catalyst contained therein. Generally, the resistance value of the gas sensing layer 160 changes with the change of the content of the absorbed target gas. Therefore, the changes in the resistance value of the gas sensing layer 160 may be calculated by observing the changes in a current input into the gas sensing layer 160 through the buffer layer 150 by the electrode pair 140, so as to obtain the changes in the concentration of the target gas around the gas sensor 100.

As the gas sensing layer 160 absorbs the target gas by using a surface, the gas sensing layer 160 is always formed by sintering fine particles, so as to obtain a large surface area; however, the mechanical strength of the gas sensing layer 160 is thus weak. On the other hand, the insulating film 120 usually has fine texture and has good mechanical strength, but at the same time, has a large coefficient of thermal expansion. The heating unit 130 functions to raise the temperature of the gas sensing layer 160, so as to increase the level of changes in the resistance value of the gas sensing layer 160 due to changes in the concentration of the target gas; however, breakage of the insulating film 120 or damage of an interface between the insulating film 120 and the gas sensing layer 160 is likely to occur, thus reducing the sensitivity of gas sensing.

As a buffer layer 150 is disposed between the insulating film 120 and the gas sensing layer 160 in this embodiment, and the mechanical strength and the coefficient of thermal expansion of the buffer layer 150 are between those of the insulating film 120 and the gas sensing layer 160, the buffer layer 150 is capable of enhancing the structural strength of the gas sensor 100 above the cavity C10 and avoiding damages at a high temperature caused by the excessively large difference in the coefficients of thermal expansion of the insulating film 120 and the gas sensing layer 160, thus significantly improving the reliability of the gas sensor 100. Moreover, as at least part of the buffer layer 150 is located on the substrate 110 next to the opening P10, and even the buffer layer 150 covers the whole opening P10, the buffer layer 150 is capable of further enhancing the structural strength of the gas sensor 100 above the cavity C10. Furthermore, as the buffer layer 150 is conductive and is capable of enhancing the electronic conduction capability between the electrode pair 140 and the gas sensing layer 160, the gas sensor 100 may obtain a strong sensing signal, and thus the sensitivity of gas sensing is improved.

Figure 2:
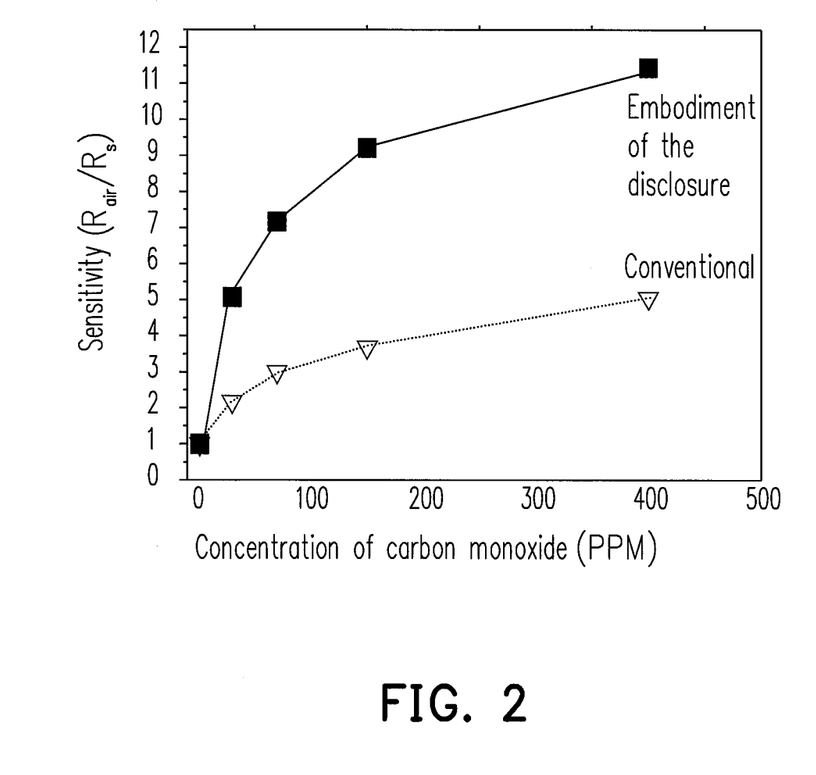
FIG. 2 shows differences in sensitivity of a gas sensor according to an embodiment of the disclosure and a conventional gas sensor.
Figure 3A:
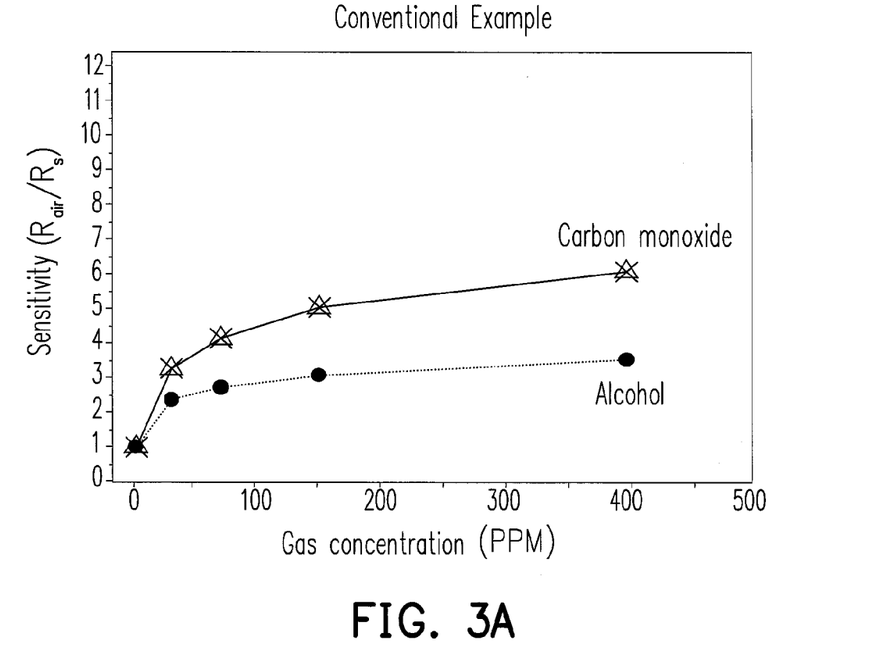
FIGS. 3A and 3B show possibilities of interference of the gas sensor according to an embodiment of the disclosure and the conventional gas sensor by non-target gases.
Figure 3B:
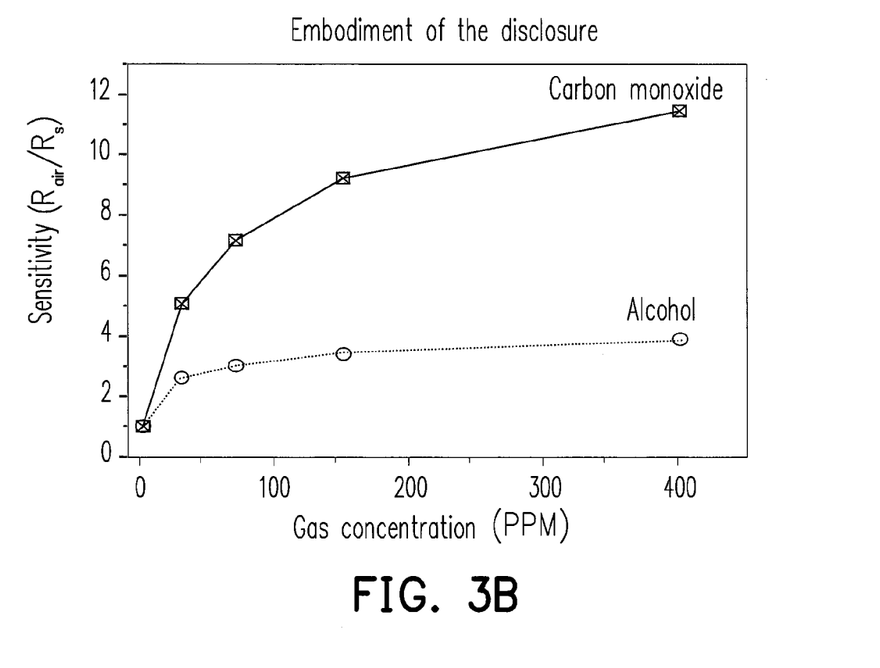
Figure 4:
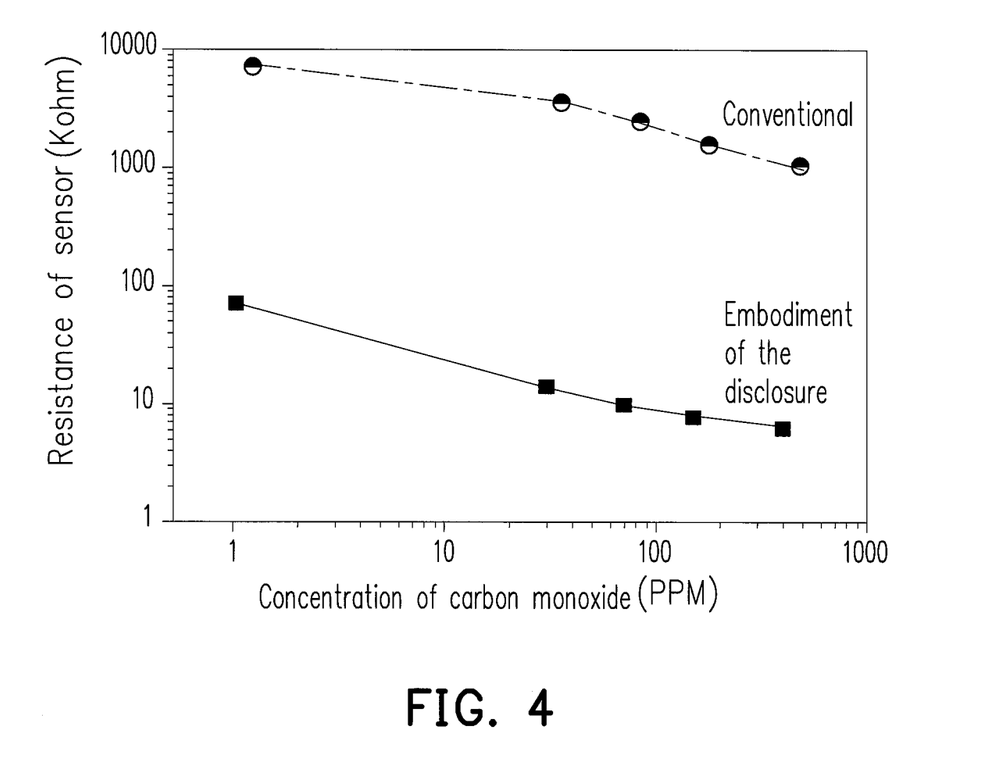
FIG. 4 shows differences in resistance values of the gas sensor according to embodiment of the disclosure and the conventional gas sensor.

It can be found from FIG. 2 that, when sensing carbon monoxide in the same working environment, the sensitivity of the gas sensor of this embodiment is much higher than that of a conventional gas sensor. It can be found from FIG. 3A that, the sensitivity of the conventional gas sensor when sensing carbon monoxide is very close to that when sensing alcohol in the same working environment (at 400 PPM, the difference is less than twice). In other words, when carbon monoxide and alcohol exist in the working environment at the same time, it is difficult to determine whether a sensing signal read by the conventional gas sensor is obtained by sensing carbon monoxide or alcohol, that is, the accuracy of the conventional gas sensor when sensing carbon monoxide is easily influenced by alcohol, and an error report may be made in an environment using alcohol in cooking. It can be found from FIG. 3B that, in the same working environment, the sensitivity of the gas sensor of this embodiment when sensing carbon monoxide is much higher than that when sensing alcohol (at 400 PPM, the difference is about three times). Therefore, when carbon monoxide and alcohol exist in the working environment at the same time, the sensing signal read by the gas sensor of this embodiment is substantially obtained by sensing carbon monoxide, that is, the accuracy of the gas sensor of this embodiment when sensing carbon monoxide is hardly influenced by alcohol. It can be found from FIG. 4 that, when testing carbon monoxide in air with a concentration of 1 PPM to 400 PPM close to background, the resistance value of the conventional gas sensor approximately changes from a high resistance value of 8000 Kohm to a high resistance value of 1000 Kohm in sensing, and the resistance value of the gas sensor of this embodiment approximately changes from a low resistance value of 80 Kohm to a low resistance value of 5 Kohm in sensing, and the gas sensor of this embodiment is suitable for a product design of a conventional simple measurement circuit. Therefore, the embodiment of the gas sensor of the disclosure has good sensing sensitivity and practicability meeting demands for electronic products.

The gas sensing layer 160 according to an embodiment of the disclosure is, for example, a sintered mixture of nanoparticles, micronparticles, and a nano-catalyst, and the structure formed by sintering the powder has good thermal expansion resistant effect. By bonding nanoparticles and micronparticles with large size difference, good bonding strength is obtained without getting loose, a large surface area is obtained, the crystal interface is reduced, and the resistance value is reduced, thus improving the sensing sensitivity. The material of the nanoparticles and the micronparticles may comprise at least one selected from the group consisting of tin oxide, iron oxide, tungsten oxide, indium oxide, zinc oxide, cobalt oxide, and other suitable materials. Moreover, the material of the nano-catalyst may comprise at least one selected from the group consisting of cobalt oxide, copper oxide, gold, palladium, platinum, copper, nickel, rhodium, and other suitable materials. Furthermore, the particle size ratio of the nanoparticles and the micronparticles is, for example, between 1:5 and 1:300. Additionally, the particle size of the nanoparticles is, for example, between 10 nm and 300 nm, and the particle size of the micronparticles is, for example, between 0.1 μm and 5 μm. Furthermore, the weight ratio of the nanoparticles and the micronparticles is, for example, 1:10.

The buffer layer 150 according to an embodiment of the disclosure is, for example, a sintered mixture of nanoparticles, micronparticles, and doped particles. The doped particles function to impart a capability of electrical signal transmission to the buffer layer 150. The difference between the buffer layer 150 and the gas sensing layer 160 mainly lies in whether a nano-catalyst is provided, and the process for preparing the gas sensing layer 160 has one more step than that for preparing the buffer layer 150, which will be described in detail later. Furthermore, the material of the nanoparticles and the micronparticles may respectively comprise at least one selected from the group consisting of tin oxide, iron oxide, tungsten oxide, indium oxide, zinc oxide, cobalt oxide, and other suitable materials. Moreover, the material of the doped particles may comprise at least one selected from the group consisting of antimony oxide, indium oxide, and other suitable materials. Additionally, the particle size ratio of the nanoparticles and the micronparticles is, for example, between 1:5 and 1:300. Moreover, the particle size of the nanoparticles is, for example, between 10 nm and 300 nm, and the particle size of the micronparticles is, for example, between 0.1 μm and 5 μm. Furthermore, the weight ratio of the nanoparticles and the micronparticles is, for example, 1:10.

The substrate 110 according to an embodiment of the disclosure is, for example, a silicon substrate, and the material of the insulating film 120 comprises, for example, at least one selected from the group consisting of silicon nitride, silicon oxide, silicon oxynitride, aluminum oxide, and other suitable materials. An insulating film 120 may also be disposed on the second surface 114 of the substrate 110. Although the heating unit 130 is embedded in the insulating film 120, the heating unit 130 may include a pad 132 that is not covered by the insulating film 120 to serve as a power input path.

Figure 5A:
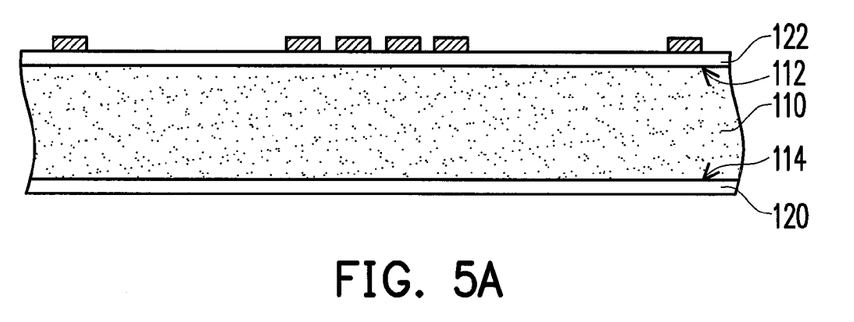
FIGS. 5A to 5I show a flow of a fabricating method of a gas sensor according to an embodiment of the disclosure.
Figure 5B:
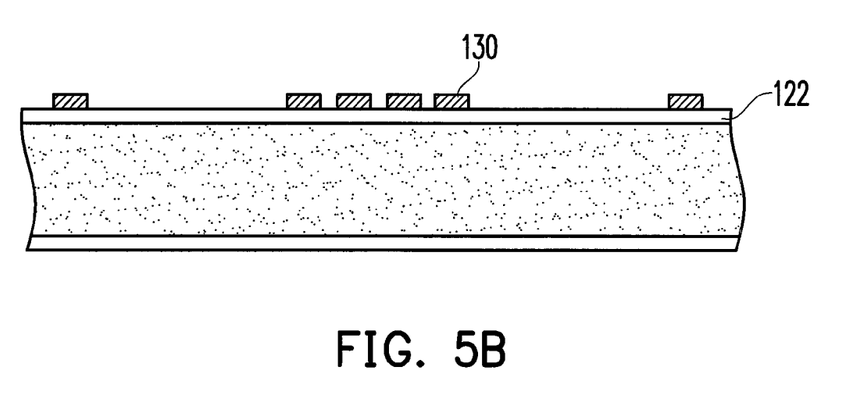
Figure 5C:
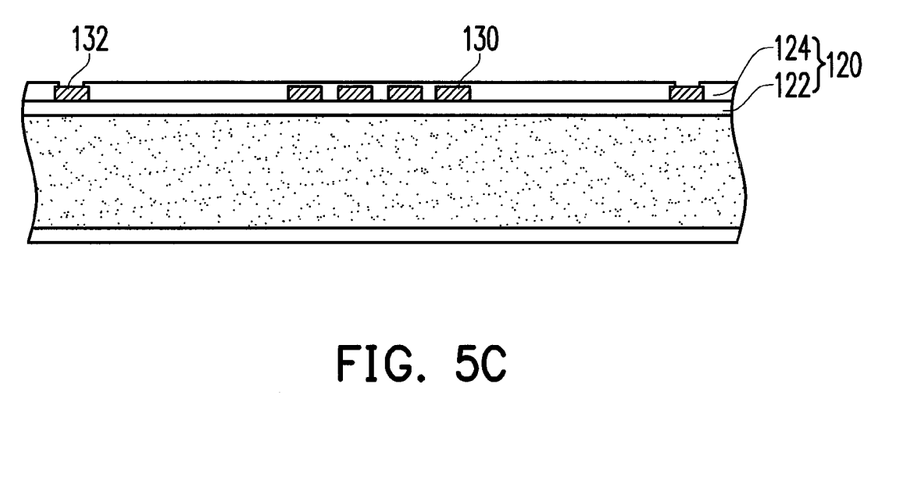

FIGS. 5A to 5I show a flow of a fabricating method of a gas sensor according to an embodiment of the disclosure. Referring to FIG. 5A, a fabricating method of a gas sensor in this embodiment includes the following steps. Firstly, a first insulating film 122 is formed on the first surface 112 of the substrate 110 by a low pressure chemical vapor deposition (LPCVD) process or other suitable methods. In this embodiment, the insulating film 120 is also formed on the second surface 114 of the substrate 110. Next, referring to FIG. 5B, the heating unit 130 is formed on the first insulating film 122 by microlithography or other suitable methods. Then, referring to FIG. 5C, a second insulating film 124 is formed on the first insulating film 122 by a plasma enhanced chemical vapor deposition (PECVD) process or other suitable methods. The second insulating film 124 covers the heating unit 130, that is, the heating unit 130 is sandwiched between the first insulating film 122 and the second insulating film 124. The first insulating film 122 plus the second insulating film 124 is equivalent to the insulating film 120 located on the first surface 112 in FIG. 1. Moreover, the second insulating film 124 may be patterned according to requirements, so as to expose the pad 132 of the heating unit 130. Definitely, the steps in FIGS. 5A to 5C may also be completed by other methods, as long as the insulating film 120 and the heating unit 130 are formed on the first surface 112 of the substrate 110.

Figure 5D:
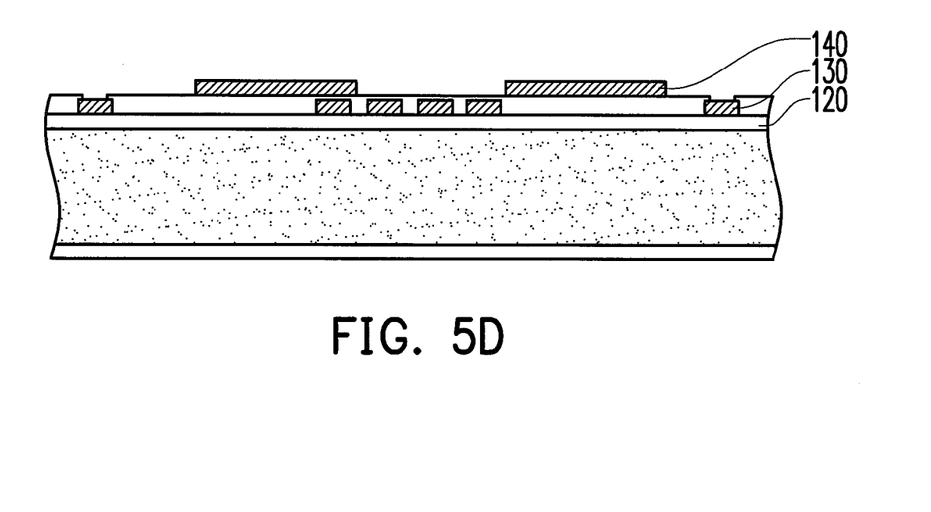
Figure 5E:
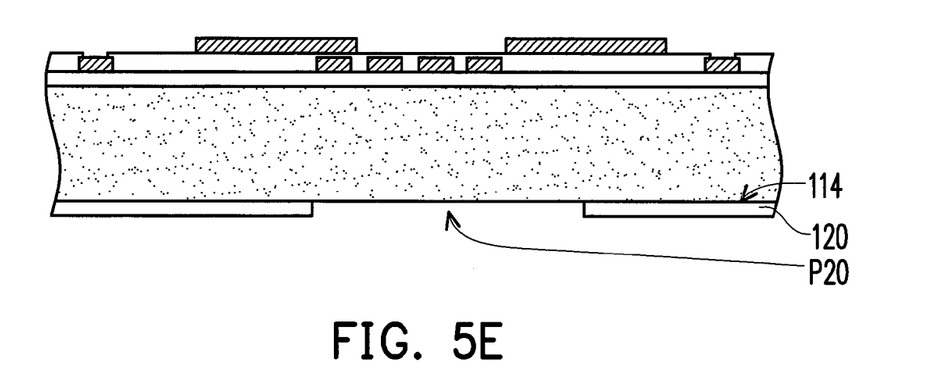

Next, referring to FIG. 5D, the electrode pair 140 is formed on the insulating film 120 by microlithography or other methods. The insulating film 120 electrically separates the electrode pair 140 from the heating unit 130. Then, referring to FIG. 5E, the insulating film 120 on the second surface 114 is selectively patterned, so as to form an opening P20. The opening P20 is used for defining the position of the cavity which is formed later, so as to serve as a positioning reference in the subsequent process.

Figure 5F:
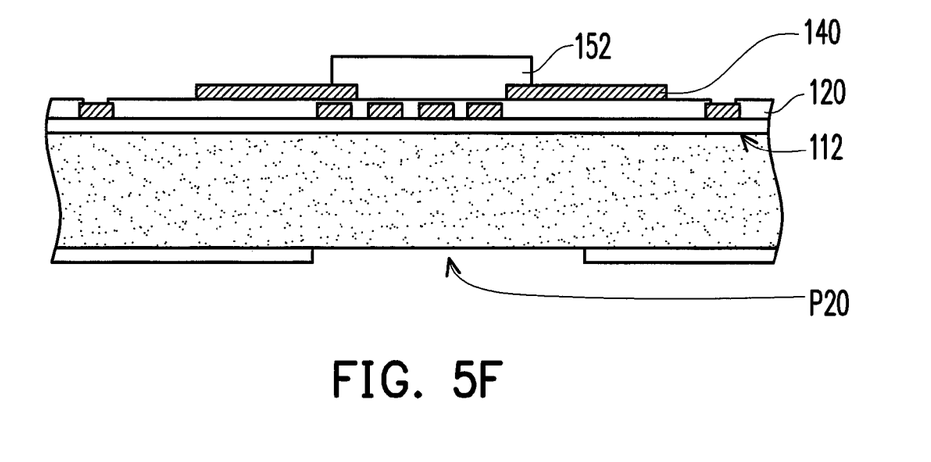

Next, referring to FIG. 5F, a layer of buffering material 152 is disposed on the insulating film 120 on the first surface 112 by screen printing or other methods. The position of the buffering material 152 is, for example, above the opening P20.

Figure 5G:
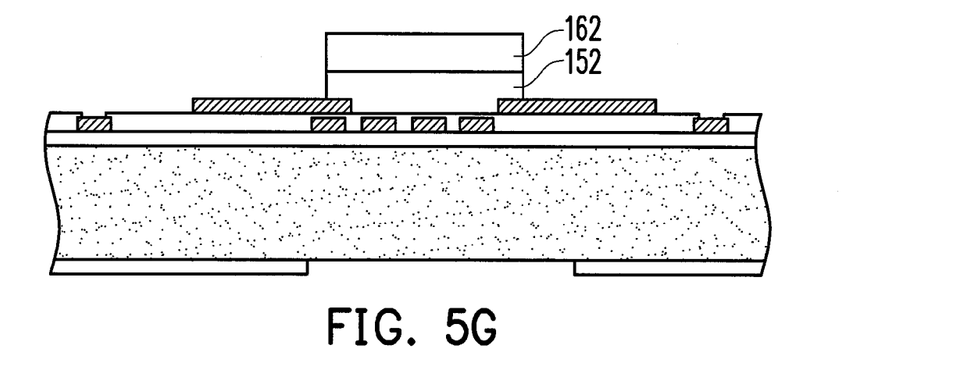
Figure 5H:
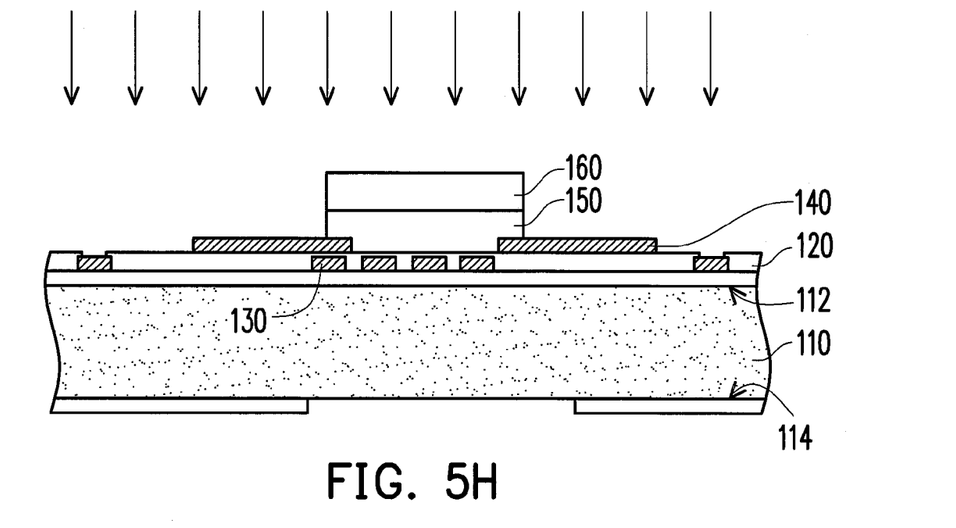

Then, referring to FIG. 5G, a layer of gas sensing material 162 is disposed on the layer of buffering material 152 by screen printing or other methods. Then, the layer of buffering material 152 and the layer of gas sensing material 162 in FIG. 5G are sintered, so as to form the buffer layer 150 and the gas sensing layer 160 in FIG. 5H respectively. When sintering the layer of buffering material 152 and the layer of gas sensing material 162 in FIG. 5G, the sintering time is, for example, between 15 minutes and 90 minutes, and the sintering temperature is, for example, between 450° C. and 650° C. The buffer layer 150 is located above the heating unit 130 and electrically connected to the electrode pair 140, and the gas sensing layer 160 has a nano-catalyst therein.

Figure 5I:
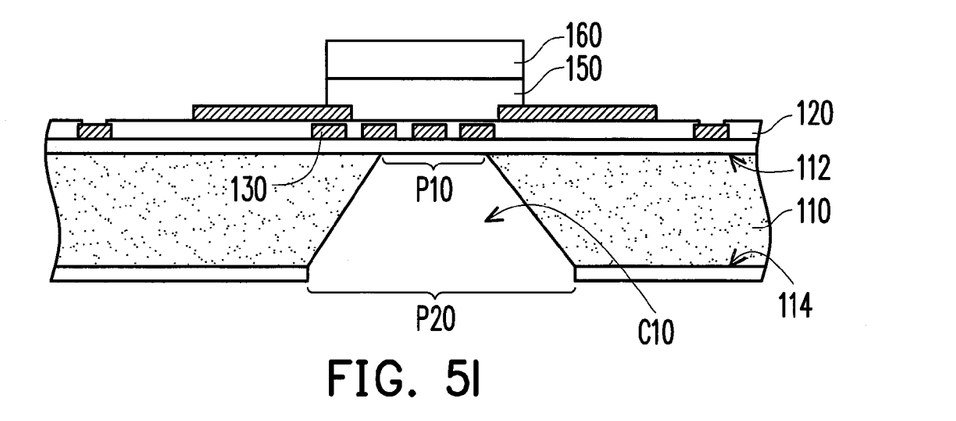

Next, referring to FIG. 5I, the substrate 110 is etched from a region of the second surface 114 of the substrate 110 exposed by the opening P20, so as to form the cavity C10. The cavity C10 has the opening P10 at the first surface 112 of the substrate 110, but the insulating film 120 covers the opening P10, and the heating unit 130 is approximately located above the opening P10. It should be noted that, at least part of the orthogonal projection of the buffer layer 150 on the first surface 112 is located on the substrate 110 next to the opening P10. In other words, without the insulating film 120, the buffer layer 150 will bridge over the substrate 110 around the opening P10. The orthogonal projection of the buffer layer 150 on the first surface 112 may completely cover the opening P10, or merely cover partial region of the opening P10. The above design aims to allow the buffer layer 150 to help the insulating film 120 resist possible damages caused by thermal stresses.

Figure 6:
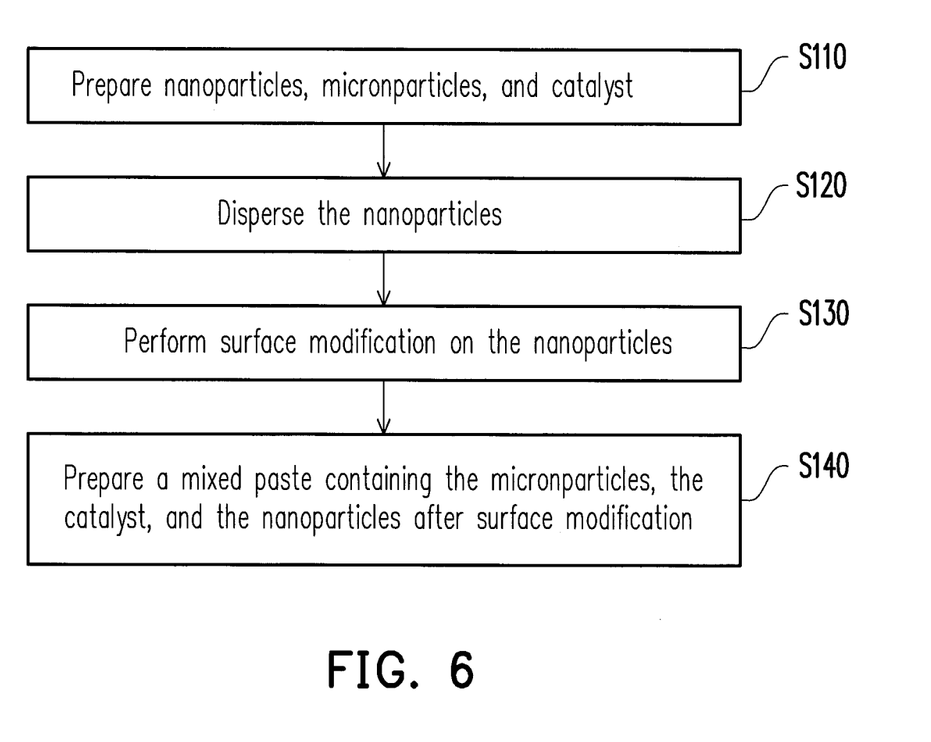
FIG. 6 shows a method for preparing a gas sensing material in FIG. 5G.

FIG. 6 shows a method for preparing a gas sensing material in FIG. 5G. The method for preparing the gas sensing material includes the following steps. Firstly, in Step 110, nanoparticles, micronparticles, and a nano-catalyst are prepared. Next, in Step S120, the nanoparticles are mixed into a solvent for dispersing the nanoparticles, so as to prevent that the nanoparticles are aggregated and cannot be evenly mixed with the micronparticles in subsequent steps. Then, in Step S130, surface modification is performed on the nanoparticles by irradiating the nanoparticles in a solution containing the nano-catalyst and the nanoparticles with ultraviolet to cause photoreaction deposition or other methods. Thereafter, in Step S140, a mixed paste containing the micronparticles, the nano-catalyst, and the nanoparticles after surface modification, is prepared. The bonding strength of the nanoparticles and the nano-catalyst is good as the nanoparticles have been subjected to surface modification, and thus the sensing properties of the gas sensing material are significantly improved. Furthermore, as the gas sensing material is formed by mixing the nanoparticles and the micronparticles, the sintering temperature does not need to be excessively high, and thus the damages on the gas sensor that may be caused by high temperature sintering may be avoided.

A method for preparing the buffering material is to form a mixed paste by mixing micronparticles, doped particles, and nanoparticles. Similarly, before preparing the mixed paste, the nanoparticles may be mixed into a solvent for dispersing the nanoparticles. The difference between the methods for preparing the buffering material and the gas sensing material in steps lies in that the method for preparing the gas sensing material has one more step of performing surface modification on the nanoparticles.

In view of the above, according to the gas sensor and the fabricating method thereof in the disclosure, the buffer layer is disposed to enhance the overall mechanical strength, so as to avoid high-temperature failure, the overall resistance value is reduced, and the signal strength is improved, thereby improving the sensing sensitivity.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A gas sensor, comprising:
   a substrate, provided with a first surface, a second surface opposite to the first surface, and a cavity, wherein the cavity is provided with an opening at the first surface;
   an insulating film, disposed on the first surface and covering the opening;
   a heating unit, located above the opening;
   an electrode pair, disposed on the insulating film and electrically separated from the heating unit;
   a buffer layer, disposed on the insulating film and located above the heating unit, wherein the buffer layer is electrically connected to the electrode pair, the buffer layer is a sintered mixture of nanoparticles, micronparticles, and doped particles, and at least part of an orthogonal projection of the buffer layer on the first surface is located on the substrate next to the opening; and
   a gas sensing layer, disposed on the buffer layer and provided with a nano-catalyst therein.

2. The gas sensor according to claim 1, wherein the gas sensing layer is a sintered mixture of nanoparticles, micronparticles, and a nano-catalyst.

3. The gas sensor according to claim 2, wherein a material of the nanoparticles and the micronparticles respectively comprises at least one selected from the group consisting of tin oxide, iron oxide, tungsten oxide, indium oxide, zinc oxide, and cobalt oxide.

4. The gas sensor according to claim 2, wherein a material of the nano-catalyst comprises at least one selected from the group consisting of cobalt oxide, copper oxide, gold, palladium, platinum, copper, nickel, and rhodium.

5. The gas sensor according to claim 2, wherein a particle size ratio of the nanoparticles and the micronparticles is between 1:5 and 1:300.

6. The gas sensor according to claim 2, wherein a particle size of the nanoparticles is between 10 nm and 300 nm, and a particle size of the micronparticles is between 0.1 μm and 5 μm.

7. The gas sensor according to claim 2, wherein a weight ratio of the nanoparticles and the micronparticles is 1:10.

8. The gas sensor according to claim 1, wherein a material of the nanoparticles and the micronparticles restively comprises at least one selected from the group consisting of tin oxide, iron oxide, tungsten oxide, indium oxide, zinc oxide, and cobalt oxide.

9. The gas sensor according to claim 1, wherein a material of the doped particles comprises at least one selected from the group consisting of antimony oxide and indium oxide.

10. The gas sensor according to claim 1, wherein a particle size ratio of the nanoparticles and the micronparticles is between 1:5 and 1:300.

11. The gas sensor according to claim 1, wherein a particle size of the nanoparticles is between 10 nm and 300 nm, and a particle size of the micronparticles is between 0.1 µm and 5 µm.

12. The gas sensor according to claim 1, wherein a weight ratio of the nanoparticles and the micronparticles is 1:10.

13. The gas sensor according to claim 1, wherein the substrate is a silicon substrate.

14. The gas sensor according to claim 1, wherein a material of the insulating film comprises at least one selected from the group consisting of silicon nitride, silicon oxide, silicon oxynitride, and aluminum oxide.

\* \* \* \* \*